US006671051B1

(12) United States Patent
Nikoonahad et al.

(10) Patent No.: US 6,671,051 B1
(45) Date of Patent: *Dec. 30, 2003

(54) APPARATUS AND METHODS FOR DETECTING KILLER PARTICLES DURING CHEMICAL MECHANICAL POLISHING (75) Inventors: Mehrdad Nikoonahad, Menlo Park, CA (US); Anantha R. Sethuraman, Palo Alto, CA (US); Guoheng Zhao, Milpitas, CA (US)

(73) Assignee: KLA-Tencor, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/556,238

(22) Filed: Apr. 24, 2000

Related U.S. Application Data (63) Continuation-in-part of application No. 09/396,143, filed on Sep. 15, 1999.

(51) Int. Cl.⁷ .............................................. G01N 21/55
(52) U.S. Cl. ..................................................... 356/445
(58) Field of Search ................... 356/445, 237.3–237.8, 356/335–343, 600–613; 250/227.28, 208.2; 134/149; 438/16, 691, 692, 693, 690, 754, 745; 216/86, 38, 89

(56) References Cited

U.S. PATENT DOCUMENTS

| 4,218,144 A | * | 8/1980 | Whitehouse et al. ........ 356/446 |
| 4,306,835 A | | 12/1981 | Hurley ........................ 415/118 |
| 4,544,446 A | | 10/1985 | Cady |

(List continued on next page.)

FOREIGN PATENT DOCUMENTS

| EP | 0738561 A1 | 10/1996 | |
| EP | 0824995 A1 | 2/1998 | |
| EP | 0881484 A2 | 12/1998 | |
| EP | 0886184 A3 | 12/1998 | ............. G03F/7/20 |
| EP | 0886184 A2 | 12/1998 | ............. G03F/7/20 |
| EP | 0890416 A2 | 1/1999 | |
| WO | WO 95/18353 | 7/1995 | |
| WO | WO 98/05066 | 2/1998 | |
| WO | 0881040 A2 | 12/1998 | |
| WO | WO 99/02970 | 1/1999 | |
| WO | WO 99/23449 | 5/1999 | |

OTHER PUBLICATIONS

Mehrdad Nikoonahad, Shing Lee, and Haiming Wang, "Non–Contract System for Measuring Film Thickness", U.S. patent application Ser. No. 09/028,417, filed Feb. 24, 1998, pp. 43.

Mike Berman, Thomas Bippy, and Alan Smith, "Review of In Situ & In–Line Detection for CMP Applications", Semiconductor Fabtech, 8th Edition, www.fabtech.org, pp. 8.

Thomas Bippy and Karey Holland, "Endpoint Detection for CMP", Journal of Electronic Materials, vol. 27, No. 10, 1998, pp. 1073–1081.

Primary Examiner—Tu T. Nguyen
(74) Attorney, Agent, or Firm—Beyer, Weaver & Thomas, LLP.

(57) ABSTRACT

Disclosed is a system for detecting anomalies associated with a sample. The system includes an objective arranged proximate to a sample while the sample is undergoing chemical mechanical polishing and a beam source arranged to generate an incident beam and direct the incident beam through the objective and toward the sample while the sample is undergoing chemical mechanical polishing. The system also includes a sensor arranged to detect a scattered beam reflected from at least one anomaly associated with the sample while the sample is undergoing chemical mechanical polishing, the scattered beam being in response to the incident beam. The scattered beam indicates a characteristic of the anomaly, such as particle size.

37 Claims, 5 Drawing Sheets

U.S. PATENT DOCUMENTS

| | | |
|---|---|---|
| 4,672,196 A | 6/1987 | Canino |
| 4,710,030 A | 12/1987 | Tauc et al. |
| 4,778,995 A | 10/1988 | Kulpinski et al. ........ 250/327.2 |
| 5,042,951 A | 8/1991 | Gold et al. |
| 5,081,796 A | 1/1992 | Schultz |
| 5,159,412 A | 10/1992 | Willenborg et al. |
| 5,166,752 A | 11/1992 | Spanier et al. |
| 5,181,080 A | 1/1993 | Fanton et al. |
| 5,196,353 A | 3/1993 | Sandhu et al. |
| 5,413,941 A | 5/1995 | Koos et al. |
| 5,433,651 A | 7/1995 | Lustig et al. |
| 5,483,568 A | 1/1996 | Yano et al. |
| 5,596,406 A | 1/1997 | Rosencwaig et al. |
| 5,597,442 A | 1/1997 | Chen et al. |
| 5,605,760 A | 2/1997 | Roberts ....................... 428/409 |
| 5,643,050 A | 7/1997 | Chen |
| 5,647,952 A | 7/1997 | Chen |
| 5,663,797 A | 9/1997 | HSandhu |
| 5,691,253 A | 11/1997 | Kobayashi |
| 5,747,813 A | 5/1998 | Norton et al. |
| 5,872,633 A | 2/1999 | Holzapfel et al. |
| 5,883,710 A | 3/1999 | Nikoonahad et al. ..... 356/237.2 |
| 5,891,352 A | 4/1999 | Litvak .......................... 216/85 |
| 5,893,796 A | 4/1999 | Birang et al. ................ 451/526 |
| 5,900,633 A | 5/1999 | Solomon et al. |
| 5,910,842 A | 6/1999 | Piwonka-Corle et al. |
| 5,910,846 A | 6/1999 | Sandhu ........................ 356/381 |
| 5,911,619 A | 6/1999 | Uzoh et al. ..................... 451/5 |
| 5,936,733 A | 8/1999 | Sandhu et al. |
| 5,949,927 A * | 9/1999 | Tang ............................ 385/12 |
| 6,122,046 A * | 9/2000 | Almogy ................... 356/237.2 |
| 6,287,879 B1 * | 9/2001 | Gonzales et al. ............. 438/16 |

* cited by examiner

APPARATUS AND METHODS FOR DETECTING KILLER PARTICLES DURING CHEMICAL MECHANICAL POLISHING

CROSS REFERENCE TO RELATED APPLICATIONS

This application is a continuation-in-part and claims priority of U.S. Patent Application, having application Ser. No. 09/396,143 filed Sep. 15, 1999 entitled "APPARATUS AND METHODS FOR PERFORMING SELF-CLEARING OPTICAL MEASUREMENTS" by Nikoonahad et al, which application is incorporated herein by reference in its entirety for all purposes.

BACKGROUND OF THE INVENTION

The invention relates to apparatus for monitoring a chemical mechanical polishing (CMP) process. More specifically, the invention relates to detection of anomalies associated with the CMP process. Additionally, the invention relates to a CMP pad and/or platen that is configured to allow such monitoring.

A wafer surface undergoing chemical mechanical polishing (CMP) is typically polished by rubbing the wafer, which is attached to a wafer carrier, against a pad that is atop a platen. A slurry is typically used to mechanically and chemically facilitate removal of a portion of a film deposed on the wafer's surface. The pad may contain embedded abrasive materials to facilitate polishing. During CMP, a defect may appear on the wafer surface. Of course, any defect on the wafer surface has the potential of detrimentally affecting the performance of one or more chips. Additionally, the shrinking of semiconductor devices to smaller and smaller dimensions has significantly increased the sensitivity of devices to particle contamination. That is, smaller and smaller particles are now more likely to adversely affect the integrity of the device.

There is market pressure to continually reduce the costs of individual chips. Consequently, manufacturers strive to maximize their chip yield by reducing the number of defects per wafer, for example. Not only is it important to detect defects when they occur so that the wafer process may be adjusted, but it is also important to prevent defects before they occur. Accordingly, manufacturers attempt to detect the causes of defects so that the defects may be prevented.

The most likely cause of a defect is one or more "killer particles." For example, killer particles generally have a large enough size to cause a physical defect (e.g., a micro scratch, a short, or other damage) on the wafer during CMP. By way of example, one or more killer particle(s) may be rubbed against the wafer during CMP to form a scratch across the wafer surface.

Killer particles may originate from any number of sources. For example, killer particles may be present within the slurry itself. Thus, the slurry is usually inspected prior to the CMP process to detect killer particles therein. Unfortunately, killer particles may also be introduced into the slurry or onto the wafer as a result of contamination on the wafer, wafer carrier, or polishing pad. Additionally, portions of the wafer itself may break off to form killer particles.

Conventionally, if killer particles are introduced into the slurry and onto the wafer after the start of the CMP process, the killer particles are detected by removing the wafer from the CMP process to inspect off-line or ex-situ. That is, the wafer is transferred to an inspection tool. Since it is difficult and time-consuming to halt the CMP process and inspect the wafer, the wafer is only periodically inspected. As a result a killer particle may go undetected for a significant amount of time. Thus, killer particles may be detected after they have caused a defect on the wafer during the CMP process.

In summary, measurement apparatus and techniques for efficiently and reliably detecting anomalies, such as killer particles, in real time during CMP (i.e., in-situ) are needed.

SUMMARY OF THE INVENTION

Accordingly, the present invention addresses the above problems by providing apparatus and methods for detecting anomalies during the CMP process. In general terms, a hole is provided in the platen and pad of the CMP system. In one embodiment, an optical element is placed within the hole to provide an optical path for measurement of the sample and/or detection of anomalies associated with the sample. A fluid may also be flowed between the optical element and sample to clear away debris from the optical path.

In one embodiment, the invention pertains to a system for detecting anomalies associated with a sample. The system includes an objective arranged proximate to a sample while the sample is undergoing chemical mechanical polishing and a beam source arranged to generate an incident beam and direct the incident beam through the objective and toward the sample while the sample is undergoing chemical mechanical polishing. The system also includes a sensor arranged to detect a scattered beam reflected from at least one anomaly associated with the sample while the sample is undergoing chemical mechanical polishing. The scattered beam is in response to the incident beam. The scattered beam indicates a characteristic of the anomaly. In a preferred embodiment, the characteristic is particle size.

In another embodiment, an in-situ chemical-mechanical polishing apparatus for polishing a sample with a polishing agent and monitoring the sample is disclosed. The apparatus has a polishing table having a viewing opening and a sample mount arranged to hold the sample over the polishing table. The polishing table and sample mount are arranged to receive a polishing agent between the sample and the polishing table and to polish the sample by moving the polishing table and the sample mount relative to each other. The apparatus also includes an optical element proximate the viewing opening. The optical element is configured to receive an optical signal and direct it through the viewing opening to the sample. The apparatus further includes a measurement device arranged to detect a scattered beam resulting from the optical signal and at least one anomaly associated with the sample.

In another embodiment, a chemical mechanical polishing pad having a hole is disclosed. The hole is configured to receive an optical element that directs a beam towards the sample and a substantially transparent fluid flowing between the optical clement and the sample such that at least a portion adjacent to the sample is substantially cleared of debris. The optical element and the fluid direct the beam towards the sample.

In another aspect, the invention is directed towards a method of detecting anomalies on a sample. During a chemical mechanical polishing procedure being performed on a sample, an incident beam is directed towards the sample. At least one non-specular beam resulting from the incident beam and at least one anomaly associated with the sample is collected. The non-specular beam is analyzed to determine whether the at least one anomaly is a killer particle. In a preferred embodiment, when it is determined that the at least one anomaly is a killer particle, the chemical mechanical polishing procedure is adjusted.

These and other features and advantages of the present invention will be presented in more detail in the following specification of the invention and the accompanying figures which illustrate by way of example the principles of the invention.

BRIEF DESCRIPTION OF THE DRAWINGS

The present invention will be readily understood by the following detailed description in conjunction with the accompanying drawings, wherein like reference numerals designate like structural elements, and in which.

DETAILED DESCRIPTION OF SPECIFIC EMBODIMENTS

Reference will now be made in detail to the specific embodiments of the invention. Examples of these specific embodiments are illustrated in the accompanying drawings. While the invention will be described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

In general terms, the present invention provides mechanisms for detecting anomalies during a CMP process, or any other process where detection of killer particles is required. Any suitable apparatus may be utilized for performing in-situ killer particle detection during CMP. For example, a self-clearing objective as described in the parent patent application may be utilized. The self-clearing objective allows various optical measurements to be performed during a CMP process that results in debris that may obscure the optical measurement path. As described further below, the self-clearing objective may be coupled with a killer particle detection system and integrated within a CMP apparatus.

Figure 1:
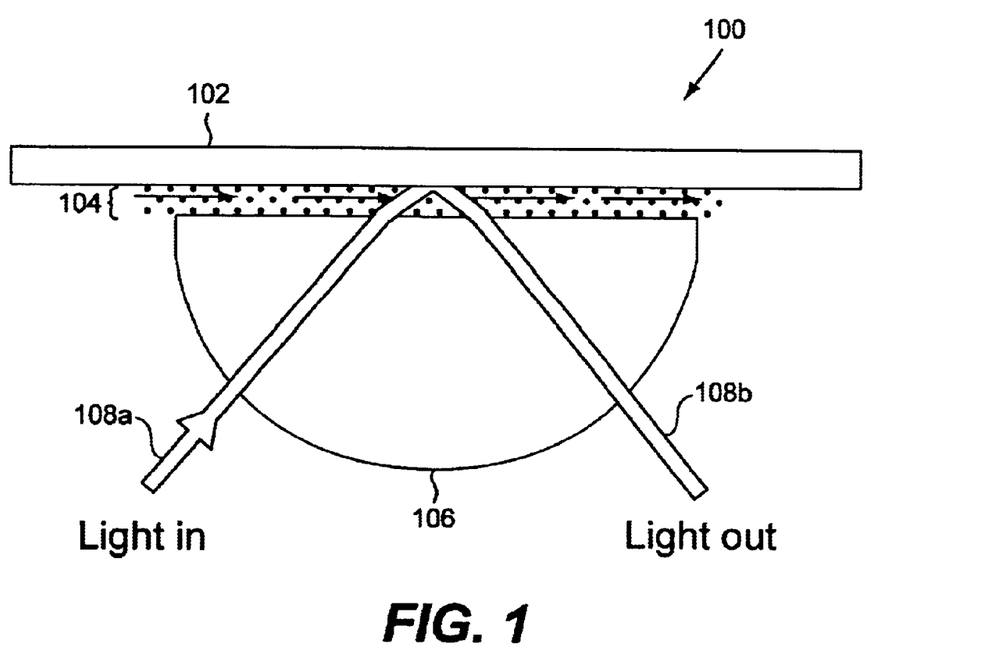
FIG. 1 is a diagrammatic representation of a self-clearing objective in accordance with one embodiment of the present invention.

FIG. 1 is a diagrammatic representation of a self-clearing objective 100 in accordance with one embodiment of the present invention. The self-clearing objective 100 includes an optical element 106 and a flowing fluid 104. The optical element 106 may work in conjunction with the flowing fluid 104 to direct an optical beam 108a toward a sample 102. A reflected optical beam 108b may pass through the flowing fluid 104 and optical element 106 to then be reflected from the sample and detected. The flowing fluid 104 also serves to clear a substantial amount of debris between the optical element 106 and sample 102. The flowing fluid 104 flows between the optical element 106 and the sample 102 such that the optical beam may pass through the optical element 106, the flowing fluid, illuminate the sample 102, and be deflected back along path 108b without significant distortion by debris. Alternatively, the fluid may be eliminated to perform an optical measurement. For example, the fluid would not be used to clear away a CMP slurry so that killer particles within the slurry may be detected. In this case, the slurry is substantially transparent or the wavelength of the beam is chosen so that the slurry is substantially transparent to the beam.

The beam may be any suitable wavelength or plurality of wavelengths of an electromagnetic radiation that can be directed, shaped, focused, collimated, or otherwise modified. In one embodiment the beam has a wavelength within the optical range (i.e., between 190 nm and 101 $\mu$m). Preferably, the beam has a wavelength in the visible range (i.e., between 400 nm and 800 nm). As it is to be used to probe the condition of a surface, the beam will be chosen to allow analysis of the surface. Accordingly, the flowing fluid 104 may have any suitable composition that is substantially transparent to the type of radiation used in the beam. For example, the fluid may be composed of water, through which a 400 nm to 1000 nm light beam may pass without significant scattering. However, when the water contains particulates (e.g., from the slurry or polishing residue), a longer wavelength (e.g., 800 to 900 nm) of light may be utilized to reduce scattering by the particulates. Alternatively, the fluid may be selected such that it is merely optically superior to the debris being cleared away (and not necessarily completely transparent to the beam). By way of further examples, the fluid may be liquid or gas, inorganic or organic, etc.

In one embodiment, the self-clearing objective is coupled with an anomaly (e.g., killer particles) detection system. The self-clearing objective may then be used to clear away debris that obscures measurements of anomalies on the sample. For example, the self-clearing objective may be coupled with various wafer measurement systems. The self-clearing objective may also be coupled with any other suitable measurement system, such as a reflectometer, an ellipsometer, an interferometer, and a pulse-echo photoacoustic system. The self-clearing objective may also be used within any sample processing apparatus that causes debris to hinder the measurement being taken of the sample. In the illustrated embodiment, the self-clearing objective is integrated within a CMP system which necessarily results in slurry and film residue blocking the measurement path to the sample.

The measurement devices may be configured in various ways. The reflectomer may measure reflectivity using multiple incident beam angles or a single beam angle. Additionally, the reflectometer may measure reflectivity at various wavelengths or a single wavelength. Likewise, the ellipsometer and anomaly detector may be configured to measure at any combination of multiple angles, a single angle, multiple wavelengths, and a single wavelength.

Several reflectivity measurement apparatus and reflectivity analysis techniques are described in U.S. Pat. No. 5,747, 813 by Norton et al and U.S. patent application Ser. No. 09/298,007 filed Apr. 22, 1999 by Wang et al. Several embodiment of ellipsometer apparatus and methods are described in U.S. Pat. No. 5,910,842 by Piwonka-Corle et al. Pulse-echo photoacoustic systems and methods are described in U.S. application Ser. No. 09/028,417 filed Feb. 24, 1998 by Nikoonahad et al and an article entitled "Picosecond Photoacoustics using Common Path Interferometry," Applied Physics Letters, vol 76, No 4, Jan. 24, 2000, by M. Nikoonahad et al. These patents, patent applications, and article are herein incorporated by reference in their entirety.

When a measurement system with a self-clearing objective is integrated or coupled with a sample processing system, the sample may be clearly monitored as it is being processed. The self-clearing objective of the measurement system provides a mechanism for clearing away debris from a viewing path to the sample. Thus, the sample may be optically monitored without debris obstructing the optical path. Some example processing systems that may utilize a measurement system having a self-clearing objective are epitaxy crystal growth, pipe cleaning, various etching processes, and various wafer processes, such as CMP.

Figure 2:
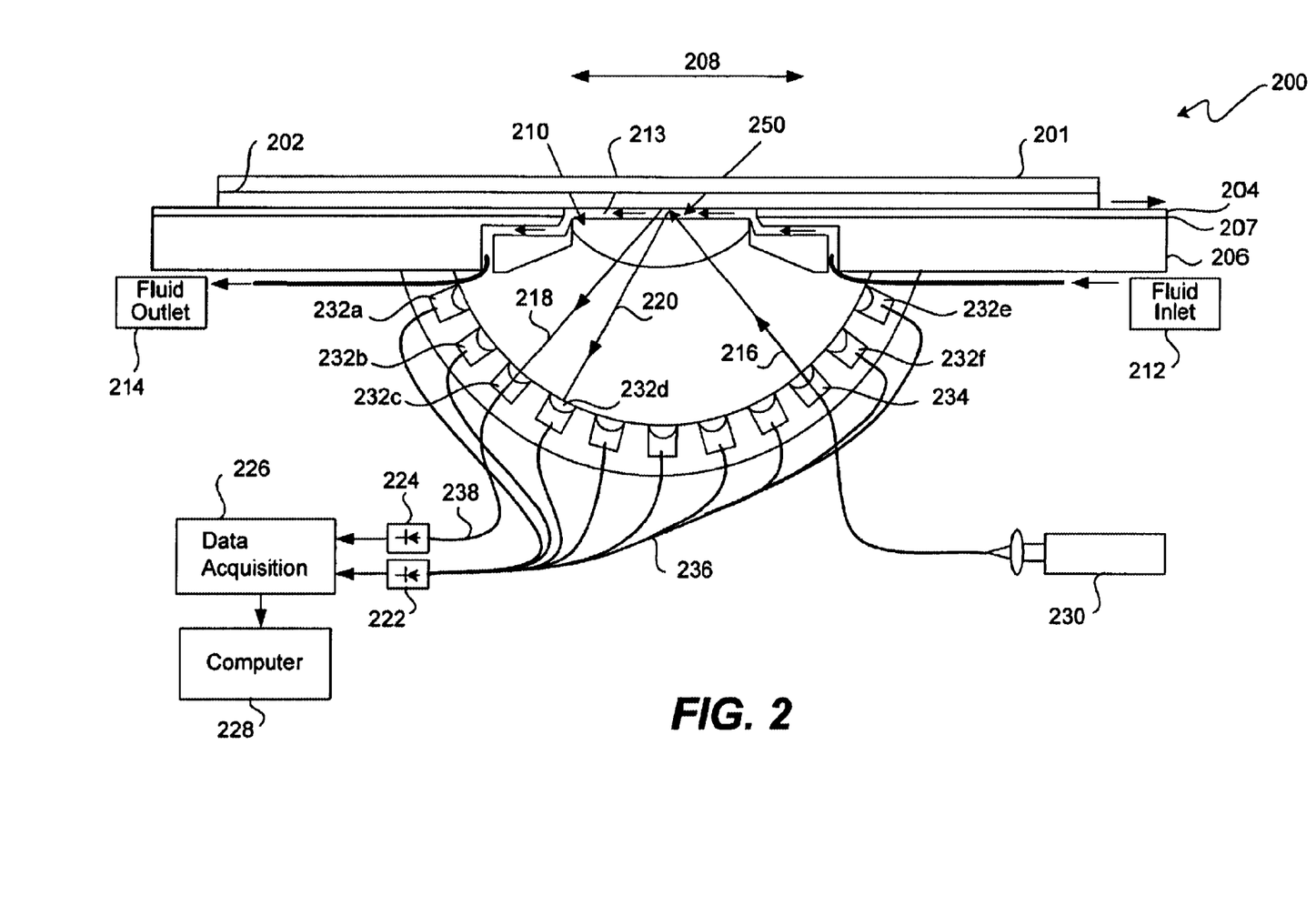
FIG. 2 is a diagrammatic representation of a section of a chemical mechanical polishing (CMP) apparatus that also provides anomaly detection capabilities in accordance with one embodiment of the present invention.

FIG. 2 is a diagrammatic representation of a section of a chemical mechanical polishing (CMP) apparatus 200 that also provides anomaly detection capabilities in accordance with one embodiment of the present invention. In the illustrated embodiment, the CMP apparatus is also operable to provide other measurements, such as reflectometry measurements for detecting a film's endpoint during CMP. As shown, the CMP apparatus 200 includes a sample holder 201 and a pad 207 and a platen 206 having a hole 208. The sample holder 201 is arranged to hold a sample 202 against the pad 207 and the platen 206. A slurry 204 and/or reactive fluid is flowed between the sample 202 and pad 207, which is atop platen 206. The pad may contain embedded abrasive particles to facilitate polishing. When the pad contains abrasive particles, the reactive fluid may work in conjunction with the abrasive particles to facilitate polishing. When the sample is moved relative to the pad 207, the slurry 204 functions to mechanically and/or chemically polish the sample 202. Of course, any suitable polishing agent may be utilized.

The hole 208 of the pad 207 and platen 206 may be configured to contain any suitable objective, such as the above-discussed self-clearing objective 100 of FIG. 1, through which optical measurements may be performed. The hole within the pad and platen may have any suitable size. For example, the hole may have a diameter in the range of about 0.1 mm to 50 mm. More preferably, the hole diameter is in the range of about 1 to 10 mm. The hole may also be any suitable shape. For example, the hole may enclose a rounded cylindrical space (or any other cylindrical or prism shaped space having parallel or non-parallel bases), a cube shaped space, a cone-shaped space, etc. Additionally, the pad may contain multiple holes. The different holes may then provide insertion of different objective or sensor types. The light from a plurality of objectives can be analyzed separately or integrated together.

The polishing results in various debris between the sample surface and the optical element 210. This debris includes slurry which is typically opaque and inhomogeneous. Additionally, a portion of the sample is polished off of the sample during polishing. This residue collects within the slurry. This collection of debris (e.g., slurry and residue) may significantly distort an optical beam that is directed at the sample surface to monitor the polishing process. For example, it may be difficult to use an optical measurement device to detect an endpoint for removal of a particular sample layer from the sample. A fluid may be utilized to clear away some of this debris so that a portion of the sample may be clearly monitored.

As shown, the self-clearing objective of FIG. 2 includes an optical element 210 and a flowing fluid 213. Any suitable mechanism may be implemented for generating the flowing fluid 213 of the self-clearing objective. As shown, the self-clearing objective also includes a fluid pump 212 and a fluid outlet 214 that generate a constant fluid flow between the optical element 210 and sample surface 202. Alternatively, a fluid pumping system may be implemented within a single device that generates flowing fluid 213. By way of a final example, a ring-shaped hole may be formed around the viewing area into the center of which the fluid is pumped. The fluid then exits through the ring-shaped hole.

The fluid pump 212 may include a control valve (not shown) for adjusting the flow rate. Likewise, the fluid outlet 214 may include a vacuum that provides some control over the fluid flow rate to the fluid outlet 214. The fluid flow rate may be adjusted for different applications or polishing conditions in order to provide different levels of clearing depending upon the specific application. For example, the fluid flow rate may depend on type of slurry, polishing speed, size of fluid reservoir, configuration of optical element, wavelength of light, concentration of slurry, amount of impact on the process, etc. As shown, a slurry 204 that is placed between the pad 207 and the sample 202 is substantially cleared away from the viewing surface of the sample 202 by the flowing fluid 213.

The fluid pump 212 may also include a sensor (not shown) arranged to determine when the sample is near the self-clearing objective. The sensor may utilize pressure, optical, or other inputs to determine sample location. The fluid flow may then be modulated as the sample is near or on top of the self-clearing objective. This arrangement clears the debris along the optical path without overly diluting the slurry adjacent to the self-clearing objective. This prevents the slurry from becoming too diluted to effectively polish the sample.

In the illustrated embodiment, an incoming beam 216 is directed towards the sample 202 by beam generator 230. The beam generator may have any suitable form for outputting an optical signal. Preferably, the beam generator 230 is in the form of a laser source. The laser source 230 may include several laser sources, such as laser diodes, or include a single laser source that is then split into multiple laser beams. The optical beams are collimated by collimators 234. A divergent beam is input into each collimator and output from the associated collimator as a substantially parallel beam. Of course, the collimator may be eliminated in certain applications, for example, when a tighter focus area on the sample is required during killer particle detection to detect relatively small sized particles (e.g., within the sub-micron range). A more tightly focused incident beam results in a stronger scattered signal.

In theory, the incoming beam 216 is then reflected off sample 202 as a reflected specular beam 218. The specular beam 218 is collected by a lens 232c that is coupled with a corresponding fiber optic cable 238. The lens 232c is placed at the angle of the reflected beam. The specular signal is then sensed by specular detector 224, which outputs a detected signal to data acquisition block 226 and computer 228. The intensity or reflectivity values of the reflected specular beam 218 may then be analyzed to determine various thickness of multiple film layers on sample 202. Any suitable reflectivity analysis may be implemented, and such techniques are well known to those skilled in the art. Several reflectivity measurement and analysis techniques are described in U.S. Pat. No. 5,747,813 by Norton et al., which patent is herein incorporated by reference in its entirety.

Reflectivity may be measured at multiple angles with slight modifications to the illustrated embodiment of FIG. 2. For example, a plurality of specular detectors (in addition to specular detector 224) may be coupled with other fiber optic cables (e.g., fiber cables coupled with lenses 232*a* and 232*b*). Measuring reflectivity at multiple angles provides several advantages over conventional in situ measurement systems that only provide measurements using a single angle of incidence. For example, an endpoint may be detected within a CMP system by comparing the relative values of reflectivity. In other words, when the reflectivity values of various incident angles are plotted, the shape of the curve may be analyzed to determine the endpoint. In contrast, conventional systems that utilize a single incident angle must analyze a single absolute reflectivity value, which value may be significantly distorted by slurry, sample residue, and possibly the condition of the objective. Because the amount of signal attenuation caused by such distortion can be impossible to gauge, the measured reflectivity may not provide an accurate account of the surface condition. Thus, the multi-angle embodiment of the invention provides a more reliable detection of the endpoint during a CMP process.

The illustrated measurement apparatus 200 is also be utilized to detect killer particles in addition to conducting reflectometry measurements. Alternatively, the apparatus 200 may be only utilized for killer particle detection. When a killer particle is present within the path of incoming beam 216, the particle acts to scatter the reflected beam from the specular beam path 218. As shown, incoming beam 216 hits killer particle 250, and a scattered beam 220 is collected by lens 232*d*. Additionally, a plurality of scattered beams may be collected by a plurality of other nonspecular lenses, such as lenses 232*a*, 232*b*, 232*e*, and 232*f*, which are coupled with fiber bundle 236. Since the lenses are arranged at multiple angles to collect scattering at multiple angles, the arrangement of FIG. 2 allows collection of scattering in a darkfield fashion, both in a forward and backward direction. The nonspecular beams (e.g., scattered beams) are collected and sensed by nonspecular detector 222. These detected scattered beams may then be analyzed by data acquisition block 226 and computer 228 to determine whether a killer particle is present.

Any suitable analysis technique may be utilized to determine the presence of killer particles. Several scattering analysis techniques for detecting killer particles are described in (1) U.S. Pat. No. 5,883,710 entitled "SCANNING SYSTEM FOR INSPECTING ANOMALIES ON SURFACES" by Nikoonahad et al., (2) U.S. patent application Ser. No. 08/904,892 entitled "SYSTEM FOR DETECTING ANOMALIES AND/OR FEATURES OF A SURFACE" by Zhao et al., and (3) U.S. patent application Ser. No. 09/070,437 entitled "A METHOD FOR INSPECTING SEMICONDUCTOR WAFERS" by Rosengaus et al. This patent and these applications are herein incorporated by reference in their entirety.

Additionally, the fluid flow 213 may be reduced or stopped during the killer particle detection so as to not substantially interfere with killer particle detection under certain conditions. For example, the flow 213 is stopped to detect killer particles within the slurry itself. In contrast, the flow 213 may continue while killer particles are being detected on the sample 202 itself. The fluid flow pressure is selected based on any suitable factor, such as the particular properties of the slurry (e.g., level of opaqueness) and particular configuration of the objective and hole (e.g., size or shape).

The detection of scattering by particles requires only one illumination or incoming beam at one wavelength. However, more incoming beams at various angles and/or various wavelengths may be utilized to provide further information for classification of killer particles. The incoming beam is preferably at an oblique angle of incidence, which appears to provide to be optimum for obtaining a high signal to noise ratio for particle scattering. A normal angle of incidence may also be used if the detection for certain types of particles requires such configuration. The specular reflected beam (e.g., 218) may also be measured and analyzed for any suitable purpose. As discussed above, the specular beam may provide reflectometry data or other information that indicates a characteristic of the sample. Additionally, the specular beam may be used to normalize the nonspecular beam during particle detection.

The specular and nonspecular detectors may have any suitable configuration for detecting optical signals. The detectors may have a same form or different forms. For example, the nonspecular detector 222 may be a Photomulitplier tubes (PMTs) or avalanche photodiodes (APDs), which are relatively sensitive to small amounts of scattered light. The data acquisition block 226 and computer 228 may have any suitable configuration of hardware and software for acquiring and analyzing data. The data acquisition block 226 may also include a radio transmitter. In this embodiment, the data acquisition block 226 receives the detected data and then digitizes and transmits the digitized data to a remote receiver and processor for further analysis. A radio transmitter may significantly reduce the number of wires within the CMP tool 200. This arrangement may be useful when one does not wish to run a significant amount of wires out of a system that is rapidly moving (e.g., a rapidly rotating CMP platen). Alternatively, a universal serial bus may be used in conjunction with a slip ring to send data from the data acquisition block 226 to the computer 228.

The optical element 210 may also be configured to tighten the angles between the incoming optical beams (e.g., the optical element is curved with respect to the incident beams). In other words, the angles between the incoming optical beams are smaller before the beams enter the optical element, than after the beams exit the optical element. Thus, the angles between the incoming beams may be wider when striking the sample (e.g., greater than 70 degrees from the normal), as compared with conventional multiple angle systems. Since the total angle spread of the incoming beams is smaller, the number of optical beams that are input through the optical element 210 may be enhanced, as compared with conventional systems.

The collection of scattered light by killer particles may be implemented in any suitable manner, besides the embodiment of FIG. 2. For example, the scattered beams of the multiple angle fiber cables may be separately detected and analyzed to provide information regarding the angular distribution of the scattered light. This information may then be used to identify both the size and the type of the particles.

Figure 3:
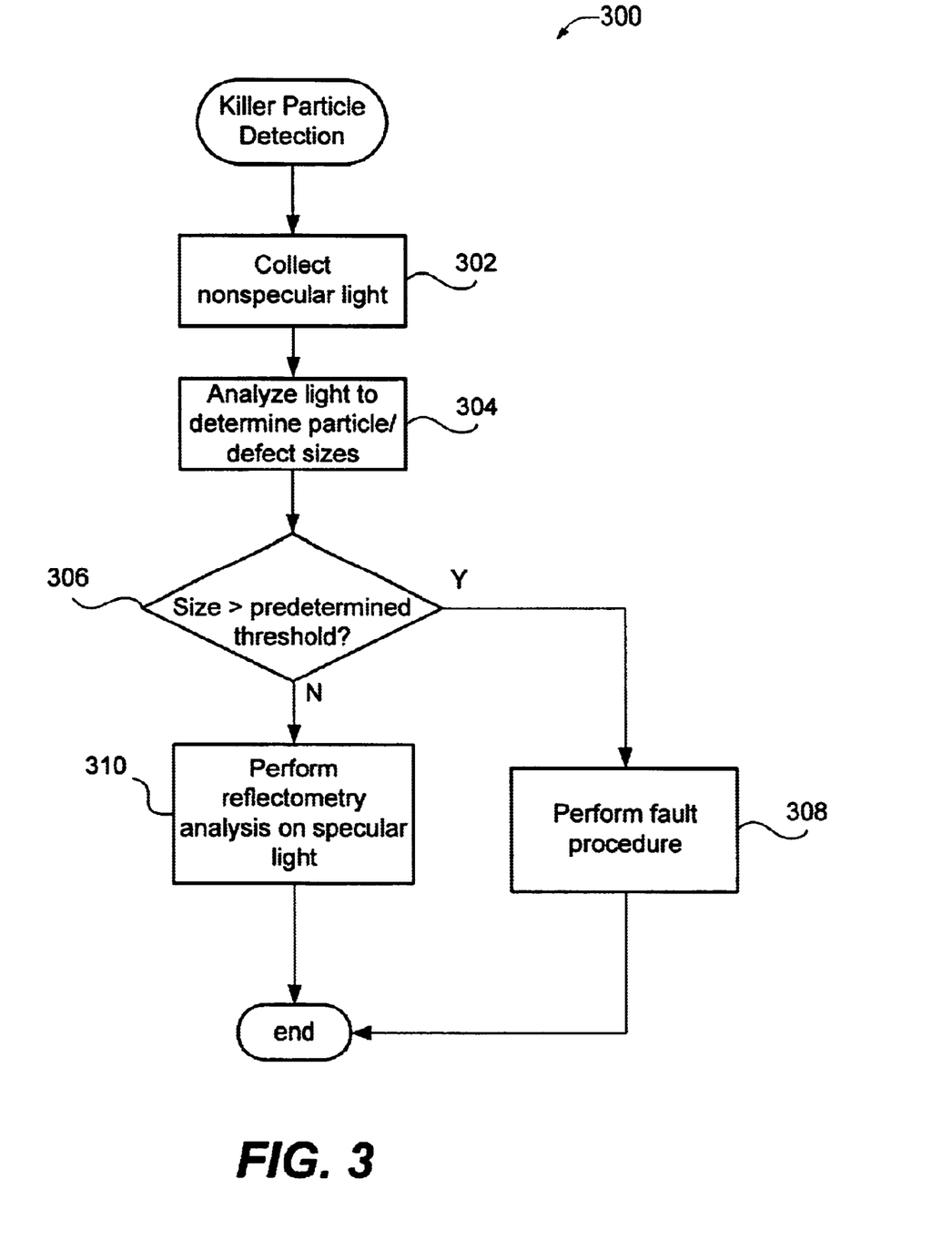
FIG. 3 is a flow chart illustrating a process for detecting anomalies in accordance with one embodiment of the present invention.

FIG. 3 is a flow chart illustrating a process 300 for detecting anomalies in accordance with one embodiment of the present invention. Initially, scattered nonspecular light is collected (302). The intensity of the scattered light is related to the size of the particle. Thus, a particle size may be determined by the intensity of the scattered light (304). It is then determined whether the particle size exceeds a predetermined threshold (306). If a particles exceeds the predetermined threshold, any suitable root cause corrective action or procedures (e.g., fault procedures) may then be implemented (308). In one embodiment, an analytical linkage or APC (automatic process control) methodology in conjunction with specific test patterns is utilized to facilitate such root cause corrective action. For example, the computer 228 sends a warning so that the CMP process may be brought under control or stopped. However, if the particle size does not exceed the predetermined threshold, the CMP procedure may continue normally. In the illustrated embodiment, reflectometry analysis is conducted on the specular light (310) to detect endpoint(s) of films that are currently being polished.

Figure 4:
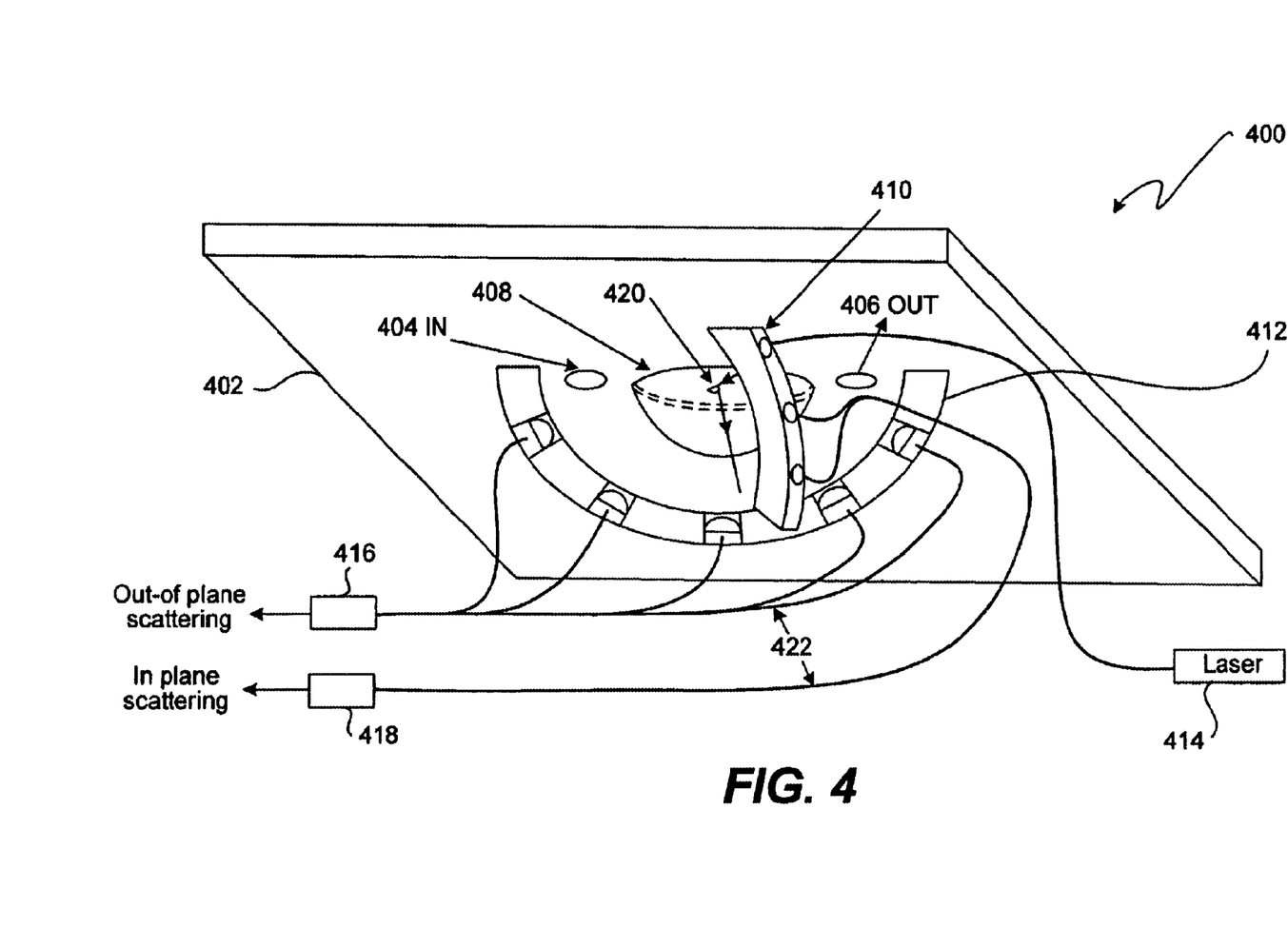
FIG. 4 is a diagrammatic representation of a section of a chemical mechanical polishing (CMP) apparatus that provides anomaly detection capabilities in accordance with a second embodiment of the present invention.

FIG. 4 is a diagrammatic representation of a section of a chemical mechanical polishing (CMP) apparatus 400 that provides anomaly detection capabilities in accordance with a second embodiment of the present invention. In this embodiment, scattered light is collected within multiple planes. As shown, the CMP apparatus 400 includes a first arc 410 and a second arc 412 residing in a different plane than the first arc 410. Both arcs are substantially centered over an optical element 408 inserted within a hole of the pad and platen 402. An incident beam is generated from laser source 414. The incident beam is directed through the first arc 410, the optical element 408, and the hole of the pad and platen 402 to an underlying sample undergoing CMP.

A first set of lenses are arranged in the first arc 410 to collect light scattered in a same plane as the incident beam. For clarity, only half of the in-plane arc 410 is shown. A second set of lenses are arranged in the second arc 412 to collect scattered light within a different plane than the incident beam. Both of the in-plane and out-of-plane scattered light is collected in fiber bundle 422. The in-plane scattered light goes to PMT detector 418, while the out-of-plane scattered light goes to PMT detector 416. One or both of the arcs 410 and 412 may be movable to collect light within various planes. For example, the out-of-plane arc 412 pivots around a center of the optical element 408.

Any suitable method may be implemented for analyzing the in-plane and out-of-plane scattered light to detect killer particles, and such techniques are well known to those skilled in the art. Several techniques are described in the above-referenced U.S. Pat. No. 5,883,710. When scattered light from multiple planes are used, reliability and accuracy of the killer particle detection are significantly enhanced. The reason for this is that the angle distribution of the scattered light depends on the stationary particle's size and/or shape.

As discussed above, reflectometry measurements may also be obtained with the CMP apparatus 400 of FIG. 4. For example, one of the lenses on the in-plane axis 410 may be positioned to receive a specular return beam. The specular return beam may then be detected and analyzed to determine a characteristic of the sample, such as film thickness or endpoint.

Additionally, debris may be cleared away from the optical path during killer particle detection and/or reflectometery measurements. As shown, fluid may enter through hole 404 and exit through hole 406 of the pad and platen 402. The fluid flows between the sample and the optical element 408 and clears away debris, such as slurry. Of course, the fluid flow may be halted under certain conditions (e.g., to detect killer particles within the slurry).

Other lenses arrangements for collecting scattered light are also contemplated. The example of FIGS. 2 and 4 are merely illustrative and are not meant to limit the scope of the invention. That is, the lenses may be arranged in other configurations, besides an arc. For example, the lenses may be arranged in a straight horizontal line across the incident plane, instead of being arranged in an arc. A single lens may be utilized to collect scattered light from a single angle off the sample or may be configured to collect from multiple angles.

Figure 5:
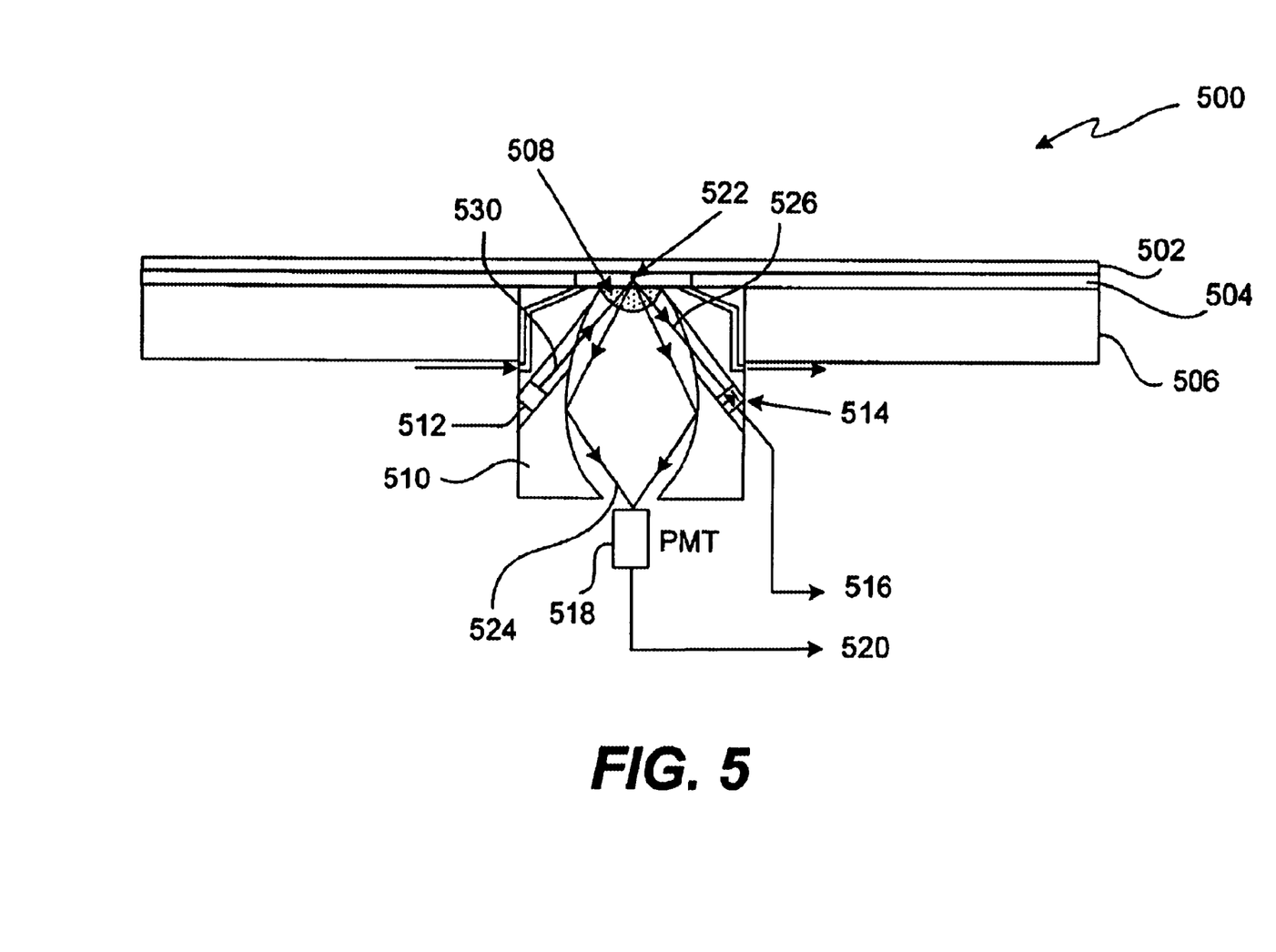
FIG. 5 is a cross sectional view of a chemical mechanical polishing (CMP) apparatus that provides anomaly detection capabilities in accordance with a third embodiment of the present invention.

FIG. 5 is a cross sectional view of a chemical mechanical polishing (CMP) apparatus 500 that provides anomaly detection capabilities in accordance with a third embodiment of the present invention. In general terms, a single optical collector is shaped to collect scattered light at multiple angles. As shown, a sample 502 undergoing CMP is moved relative to a pad and platen 506. A slurry 504 and/or reactive liquid is flowed between the sample 502 and pad (not shown), which is atop the platen 506.

The pad and platen 506 contain a hole into which an optical collector 510 and optical element 508 are inserted. An incident beam 530 is generated by source 512 and directed to the sample 502 through optical element 508. A killer particle 522 illuminated by the incident beam 530 results in scattered light 524 and/or as a specular beam 526. The optical collector may have any suitable configuration for collecting scattered beams at multiple angles. For example, the optical collector 510 may be an ellipsoidal or a compact parabolic collector (CPC). In other words, the optical collector 510 has a three dimensional ellipsoidal-shaped interior surface upon which scattered beams may be collected at multiple angles and multiple planes. The optical collector 510 is also arranged to direct the collected beams towards a single PMT detector 518. Of course, any suitable detector may be utilized for detecting scattered beams. The PMT detector 518 then outputs a scattering signal 520. This scattered signal 520 may then be analyzed to detect the presence of killer particles.

The CMP apparatus 500 may also include a second detector 514. The second detector 514 is arranged to detect a specular beam reflected from the sample 502. The specular beam may be analyzed to determine characteristics of the sample, such as film thickness or endpoint.

Although the foregoing invention has been described in some detail for purposes of clarity of understanding, it will be apparent that certain changes and modifications may be practiced within the scope of the appended claims. It should be noted that there are many alternative ways of implementing both the process and apparatus of the present invention. For example, although the present invention is described in terms of detection of killer particles, the present invention may also be utilized to detect large defects on the sample, which may act to scatter an optical beam. Additionally, the present invention may be applied in other processes, besides the described CMP process.

Accordingly, the present embodiments are to be considered as illustrative and not restrictive, and the invention is not to be limited to the details given herein, but may be modified within the scope and equivalents of the appended claims.

What is claimed is:

1. A system for detecting anomalies associated with a sample, the system comprising:

an objective arranged proximate to a sample while the sample is undergoing chemical mechanical polishing, the objective includes:

an optical element arranged to direct an incident beam towards the sample; and a fluid flow mechanism for flowing fluid which is optically transparent to the incident beam, wherein the fluid is in contact with the optical element and the sample such that only a portion of the sample is substantially flowed over by the fluid, the portion being where the incident beam is directed towards further by the fluid;

a beam source arranged to generate the incident beam and direct the incident beam through the objective and toward the sample while the sample is undergoing chemical mechanical polishing; and a sensor arranged to detect a scattered beam reflected from at least one anomaly associated with the sample while the sample is undergoing chemical mechanical polishing, the scattered beam being in response to the incident beam, wherein the scattered beam indicates a characteristic of the at least one anomaly.

2. A system as recited in claim 1, wherein the fluid substantially clears of debris at least a portion adjacent to the sample.

3. A system as recited in claim 1, wherein the characteristic of the at least one anomaly is a size value.

4. A system as recited in claim 1, wherein the at least one anomaly is a killer particle and the characteristic of the at least one anomaly is a particle type.

5. A system as recited in claim 1, further comprising a sensor arranged to detect a specular beam reflected from the sample in response to the incident beam.

6. A system as recited in claim 5 wherein the specular beam has a reflectivity value that indicates an endpoint of a film thickness on the sample and the system further comprises a computer for analyzing the reflectivity value to determine an endpoint of the film.

7. A system as recited in claim 5 further comprising a computer for normalizing the non-specular beam relative to the specular beam.

8. A system as recited in claim 1, further comprising a plurality of sensors arranged to detect a plurality of scattered beams reflected from at least one anomaly associated with the sample while the sample is undergoing chemical mechanical polishing, the plurality of scattered beams being in response to the incident beam.

9. A system as recited in claim 8, wherein the sensors are arranged to detect the scattered beams at a plurality of angles.

10. A system as recited in claim 8, wherein sensors are arranged to detect the scattered beams within a plurality of planes.

11. A system as recited in claim 8, wherein the sensors are movable to detect the scattered beams within a selected one of the planes.

12. A system as recited in claim 1, wherein the detector is a Photo-mulitplier tube (PMT) type detector.

13. A system as recited in claim 1, wherein the detector is an avalanche photodiodes (APDs) type detector.

14. A system as recited in claim 1, further comprising a transmitter for receiving the detected scattered light and outputting it to a computer for analysis.

15. A system as recited in claim 1, wherein the sensor is configured to collect a plurality of scattered beams at a plurality of angles.

16. A system as recited in claim 15, wherein the sensor is further configured to collect the plurality of beams within a plurality of planes.

17. A system as recited in claim 16, wherein the sensor is an ellipsoidal collector.

18. A system as recited in claim 16, wherein the sensor is a compact parabolic collector.

19. An in-situ chemical-mechanical polishing apparatus for polishing a sample with a polishing agent and monitoring the sample, the apparatus comprising:

a polishing table having a viewing opening;

a sample mount arranged to hold the sample over the polishing table, the polishing table and sample mount being arranged to receive a polishing agent between the sample and the polishing table and to polish the sample by moving the polishing table and the sample mount relative to each other;

an optical element proximate the viewing opening, the optical element being configured to receive an optical signal and direct it through the viewing opening to the sample;

a fluid flow mechanism for flowing fluid which is optically transparent to the optical signal, wherein the fluid is in contact with the optical element and the sample such that only a portion of the sample is substantially flowed over by the fluid, the portion being where the optical signal is directed towards further by the fluid; and a measurement device arranged to detect a scattered beam resulting from the optical signal and at least one anomaly associated with the sample.

20. An apparatus as recited in claim 19 wherein the at least one anomaly is a killer particle.

21. An apparatus as recited in claim 19, wherein the fluid substantially clears of debris at least a portion adjacent to the sample.

22. An apparatus as recited in claim 19, wherein the measurement device is further arranged to detect a specular beam reflected from the sample in response to the incident beam.

23. An apparatus as recited in claim 22 wherein the specular beam has a reflectivity value that indicates an endpoint of a film thickness on the sample and the system further comprises a computer for analyzing the reflectivity value to determine an endpoint of the film.

24. An apparatus as recited in claim 22 further comprising a computer for normalizing the non-specular beam relative to the specular beam.

25. An apparatus as recited in claim 19, wherein the measurement device is further arranged to detect a plurality of scattered beams reflected from at least one anomaly associated with the sample while the sample is undergoing chemical mechanical polishing, the plurality of scattered beams being in response to the incident beam.

26. An apparatus as recited in claim 25, wherein the measurement device is arranged to detect the scattered beams at a plurality of angles.

27. An apparatus as recited in claim 25, wherein measurement device is arranged to detect the scattered beams within a plurality of planes.

28. An apparatus as recited in claim 19, further comprising a transmitter for receiving the detected scattered beam and outputting it to a computer for analysis.

29. An apparatus as recited in claim 19, wherein the polishing agent includes one or more from a group consisting of a slurry and a reactive fluid.

30. A method of detecting anomalies on a sample, comprising:

during a chemical mechanical polishing procedure being performed on a sample, arranging an optical element to direct an incident beam towards the sample;

flowing a fluid in contact with the optical element and the sample such that only a portion of the sample is substantially flowed over by the fluid, the portion being where the incident beam is directed towards further by the fluid;

collecting at least one non-specular beam resulting from the incident beam and at least one anomaly associated with the sample; and analyzing the at least one non-specular beam to determine whether the at least one anomaly is a killer particle.

31. A method as recited in claim 30 further comprising when it is determined that the at least one anomaly is a killer particle, adjusting the chemical mechanical polishing procedure.

32. A method as recited in claim 31 further comprising when it is determined that the at least one anomaly is not a killer particle, collecting at least one specular beam resulting from the incident beam and analyzing the specular beam to determine a characteristic of the sample.

33. A method as recited in claim 32, wherein the characteristic is an endpoint of a film being polished on the sample.

34. A method as recited in claim 31, wherein flowing the fluid removes any debris that may obscure an optical path of the specular beam.

35. A method as recited in claim 31 further comprising when it is determined that the at least one anomaly is not a killer particle, collecting at least one specular beam resulting from the incident beam and using the specular beam to normalize the non-specular beam.

36. A method as recited in claim 30, wherein flowing the fluid removes any debris that may obscure an optical path of the non-specular beam.

37. A method as recited in claim 30 wherein a plurality of non-specular beams are separately collected and analyzed.

* * * * *